United States Patent [19]

Welton

[11] Patent Number: 4,835,749
[45] Date of Patent: May 30, 1989

[54] SAFE TANNING LAMP CONTROL SYSTEM

[76] Inventor: Truett T. Welton, 3635 Gardenbrook, Apt. 18200, Farmers Branch, Tex. 75234

[21] Appl. No.: 774,649

[22] Filed: Sep. 11, 1985

[51] Int. Cl.⁴ ............................................. A61N 5/06
[52] U.S. Cl. ...................... 368/10; 128/376; 128/395
[58] Field of Search .......... 128/376, 395, 396, 419 R; 315/360; 361/334, 331–333; 368/10, 90

[56] References Cited

U.S. PATENT DOCUMENTS

| | | | |
|---|---|---|---|
| 3,448,843 | 6/1969 | Mesh | 194/221 |
| 3,786,960 | 1/1974 | Young | 194/221 |
| 3,873,019 | 3/1975 | Holcomb | 377/13 |
| 3,878,377 | 4/1975 | Brunone | 377/13 |
| 3,923,134 | 12/1975 | Rezazadeh | 52/79.1 |
| 4,013,922 | 3/1977 | Van Der Meulen | 315/129 |
| 4,091,441 | 5/1978 | Ott | 315/153 |
| 4,095,139 | 6/1978 | Symonds et al. | 315/153 |
| 4,283,661 | 8/1981 | Doty | 315/129 |
| 4,312,436 | 1/1982 | Martin et al. | 194/206 |
| 4,428,050 | 1/1984 | Pellegrino | 377/20 |

Primary Examiner—Bernard Roskoski
Attorney, Agent, or Firm—T. D. Copeland

[57] ABSTRACT

A tanning studio having a tanning system, including a main control console for operation only by an attendant and a remote tanning room control for operation by a patron. A module is provide which both displays and sets the time remaining on both the console and the remote control which time is below an identified safe maximum time inherent in the system. The console includes means to only input the initial time remaining for use of the equipment, while the remote unit has means to only actuate said equipment. Both units contain means to clear the remaining time for use of the equipment Z and extinguish the lamps and a down timer for continuously displaying the time remaining.

5 Claims, 5 Drawing Sheets

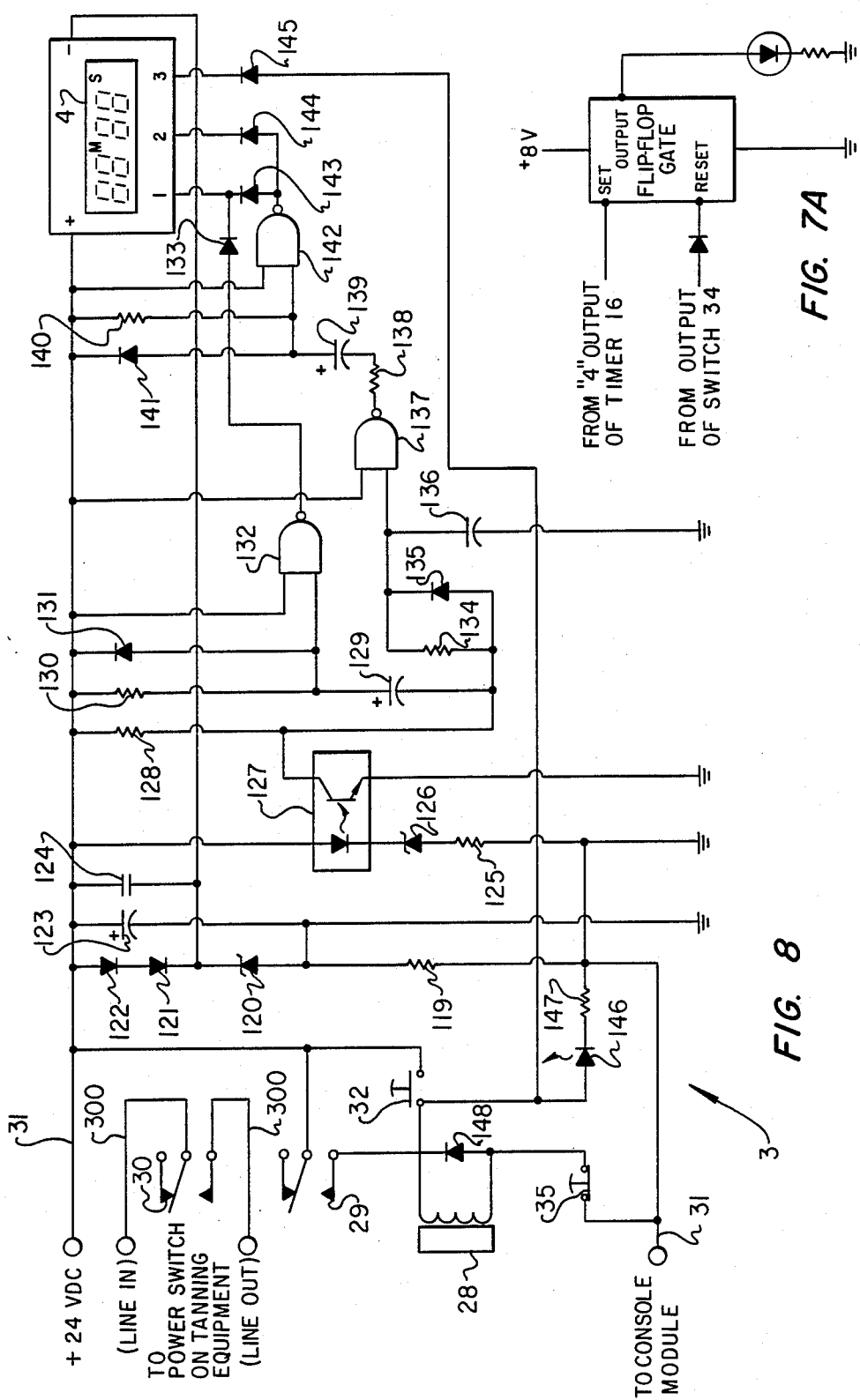

SAFE TANNING LAMP CONTROL SYSTEM

FIELD OF THE INVENTION & PRIOR ART a. Field: This invention relates generally to equipment and the control thereof, which is designed to permit the user to obtain a healthy and attractive tan without the requirement of exposure to the potentially damaging rays of natural sunlight. More specifically, this invention relates to the control circuitry necessary to permit the owner of tanning equipment to accurately measure and regulate the use of his equipment.

b. Prior Art: The following patents relate to the state of the art of equipment and control circuitry in the field of this invention, and are considered representative of the prior art:

| Patent No. | Inventor | Subject Matter |
| --- | --- | --- |
| 3923134 | Rezazadeh | Rest Accommodation Complex |
| 4013922 | Van Der Meulen | Sunlamp Device |
| 4091441 | Ott | Full-Apectrum Luminaire |
| 4279254 | Boschetti et al | Ultraviolet Light Control |
| 4283661 | Doty | Irradiation Device & Timer |
| 4428050 | Pellegrino et al | Tanning Aid |

SUMMARY OF THE INVENTION

In the industry of tanning equipment, manufacturers have endeavored to provide some type of timing control to ensure that the patron receives the correct amount of exposure time for which he has paid and that the owner/operator receives accurate compensation for his services and use of equipment.

In the past, this has been attempted largely by a mechanical manually wound timer, similar to that used by housewives, or by an electric timer operated by a coin operated mechanism.

This invention will provide an arrangement whereby the customer/patron is the only one who has control of the tanning equipment regarding the exact moment at which such equipment will become operative. And this moment will occur after said customer is lying down in the tanning bed and ready to receive his treatment. He or she will not however, be able to start the equipment until their time has been paid for and recorded by the attendant at the main console in the reception area of the tanning studio. This main console houses a plurality of individual control units that correspond, one for one, with the number of tanning beds in the tanning room area.

In the tanning system employing this invention, as in most present day tanning systems, the lamps employed are especially made to emit predominately UV-A rays, which produce the desired tanning effect in human skin without inducing burning of the skin. Another component in ultra-violet and sun light is the UV-B rays which would produce burning if they predominated the spectrum to which the patron is exposed. However, since a small amount of UV-B radiation is necessary to begin the chemical reaction in the skin for tanning, the lamps employed emit a spectrum that includes approximately 2% UV-B rays in combination with the other rays emitted.

BRIEF DESCRIPTION OF THE DRAWINGS

FIG. 7A is a fragmentary circuit diagram of an alternate embodiment with an improved alert signal display for the control system's master console.

FIG. 8 is a detail circuit diagram of the electronic circuit of the remote control unit of FIGS. 1, 4 and 5.

DETAILED DESCRIPTION OF THE PREFERRED EMBODIMENT(S)

Figure 1:
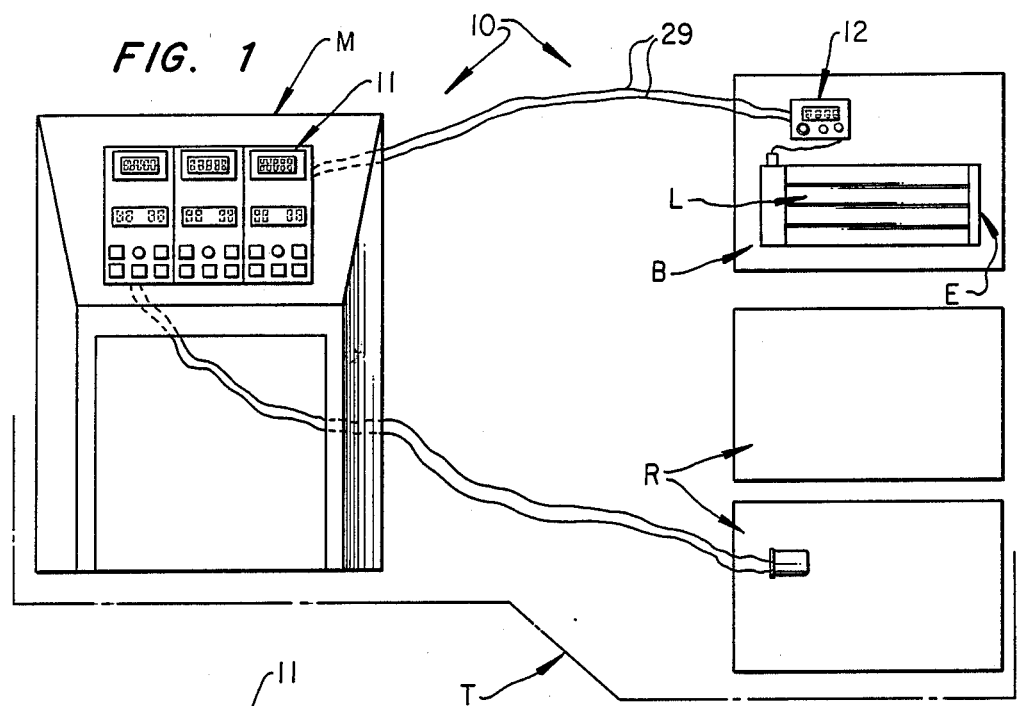
FIG. 1 represents an overall plan layout in schematic fashion of the principal components and sub-assemblies, involved in this invention, as utilized in a tanning studio.

Referring now more particularly to the characters of reference on the drawing, it will be observed in FIG. 1, that the tanning studio "T" comprises basically a series of tanning rooms "R", and a master console "M", having therein an electronic control unit(s) 2 that interconnects with a remote control unit(s) 3 in the tanning room(s) R to provide a sequential two party control arrangement for energizing and shutting off the special tanning lamps "L" associated with the tanning bed "B" in each tanning room R.

Figure 2:
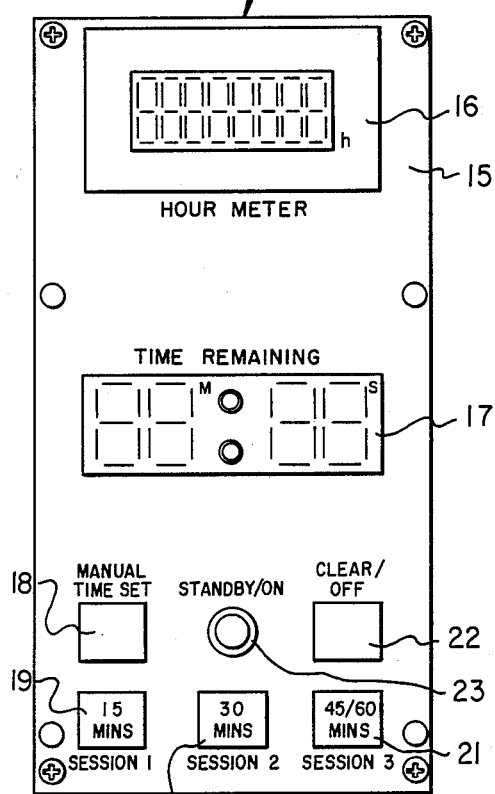
FIG. 2 is a detail front view of a control unit of FIG. 1.
Figure 3:
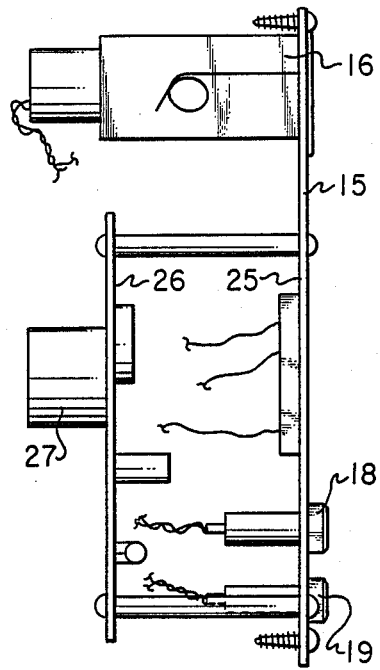
FIG. 3 is a side view of the control unit of FIG. 2.

FIGS. 2 and 3 show the details of the hardware of the control units 2, each of which includes a front panel 215 on which is mounted an hour meter display 33, that shows the total time that the tanning equipment "E" and lamp system L, with which it is associated, has been used. The reading from meter 33 permits the owner to evaluate the performance of each lamp and control system, and to schedule maintenance, and the like. Below meter 33 on the front panel 215, is located a "time remaining" display 4, which is operated by a countdown timer, 16, so, at any instant the front office attendant may determine the amount of time remaining on each unit (lamp system L and tanning bed B) of tanning equipment E. This capability will permit the attendant to schedule the starting time for the next patron relative to each unit of tanning equipment in the studio.

Below the display 4 are located a series of five pushbutton switches 10–13 and 34, and a two color element light emitting diode (LED) display assembly 223. When selected time has been entered, but not "started", it shows on display 4, and the LED display 223 shows a steady green light. This LED flashes green when the time is being entered, holds a steady green when the system is in standby, and holds a steady red light when the tanning equipment is operating. When a customer in the corresponding tanning room R puts his lamp system L into operation, his LED display turns red, and a countdown timer 20 causes his display 4 to "count down" the purchased and displayed time, until zero is reached, or until the customer or attendant cancels the remaining time and causes the time display to revert to zero. The "clear" button 34 enables the attendant to stop the operation independent of the customer's start and stop control in the tanning room R.

The side view of FIG. 3 shows the control unit 2 to be comprised of a pair of parallel spaced apart boards 215 and 226, one of which, 215, is the front panel member, which is spaced from the rear printed circuit board 226 by spacers 260. The wiring of the components of control unit 2 and the circuitry of the printed circuit board 226 is described in detail with reference to FIGS. 6–8, where it will be shown that the entire electrical contact between main control unit 2 and remote control unit 3 is through only two conductors 31.

In summary, the basic control system 1 comprises the following major structural and functional sub-systems and control units:

A. MAIN CONTROL UNIT, identified at 2, includes the following elements:

1. Down Counter & Display Driver (or countdown timer) unit 16, of FIG. 6, which through indicator display 4 shows the time remaining on the tanning equipment in use, and when initially inserted, displays the time paid for by the customer. Corresponding timers 20 are located on the remote control units 3, and each timer unit counts down from the previously entered (by manual or automatic time entry buttons 10–13) amount of time. Tanning equipment is switched on and countdown is initiated by pushing the "start" button 32 on the remote control unit 3 in the tanning room. Normally the equipment stays on while countdown takes place, and is automatically switched off when the count reaches zero, and the tanning lamps are extinguished.

2. Time Entry Controls (or pushbutton switches), identified at 10–13 on console mounted control unit 2, provide manual entry to set any desired amount of time, up to the internally programmed maximum amount of time, shown to be 60 minutes, but can be 30 minutes, since some manufacturers are only allowed to have a maximum timer setting of 30 minutes or less depending on their individual license from the Food & Drug Administration (FDA) who regulate manufacture of tanning equipment. Automatic time entry controls 11–13 comprise one or more buttons to automatically enter a preset (or, in memory) amount of time. Once a selected amount of time has been entered into any of the memories (A,B or C) and show on the display 4, the system is in the "stand-by" mode and ready to be started by depressing the "start" button 32 on the remote control unit 3 in the tanning room. However, if no time has been entered by the attendant at the entry room main console M, then the tanning equipment E and the lamps L in the tanning room cannot be turned on by the patron.

3. Clear Buttons, identified at 34 on control units 2, clear the displays 4 at the main unit 2 and also at the remote units 3 and reset all countdown timer circuits to zero, thus extinguishing all tanning lamps L. In the remote units, the clear function is activated by depressing an emergency stop or "end session" button 35.

4. Hour Meter, identified at 33 on control unit 2, counts (tabulates or totalizes) and displays the total (or cumulative) number of hours that the equipment has been used. This allows the owner to check his cash flow against usage for which time has been sold.

B. REMOTE CONTROL UNITS located in the tanning rooms, are identified at 3 and have a two wire connection 31 with the main console mounted control units 2 located in the reception area of the tanning studio. The two wires 31 carry all of the control signals back and forth between units 2 and 3. By this system, entered time is registered and displayed simultaneously on the remote unit display when it is entered initially at the main unit. Using this remote unit, the patron has direct and sole control of starting the tanning session.

Figure 4A:
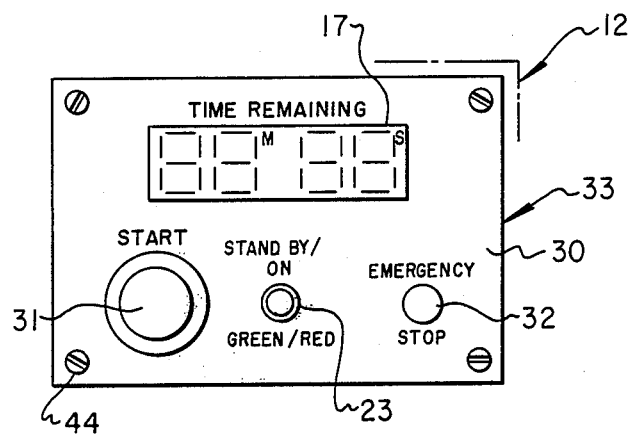
FIG. 4A is a detail front view of a remote control unit of FIG. 1.
Figure 5A:
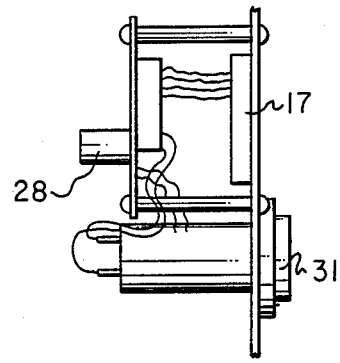
FIG. 5A is a side view of the remote control unit of FIG. 4A.
Figure 4B:
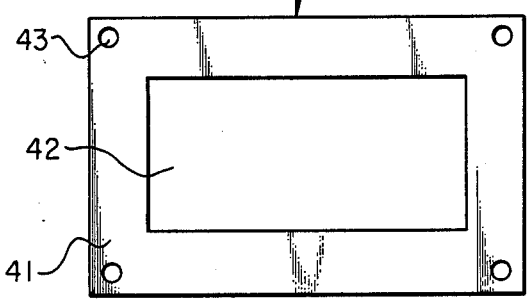
FIG. 4B is a front view of the housing for the remote control unit of FIG. 4A.
Figure 5B:
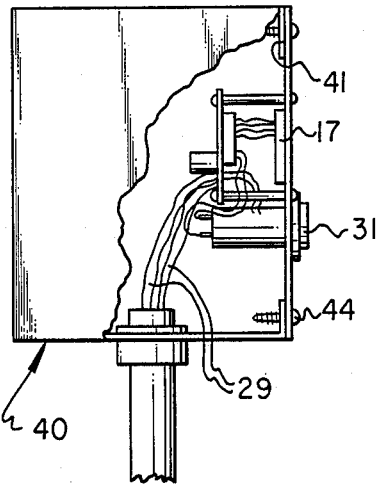
FIG. 5B is a side view, partly cut-away, of the remote control unit of FIGS. 4A–4C and 5A after assembly.
Figure 4C:
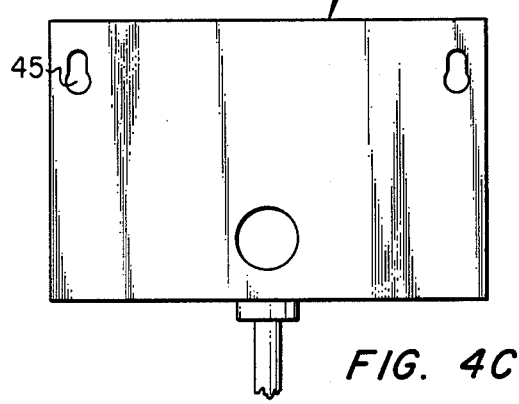
FIG. 4C is a rear view of the device of FIG. 4B.

FIGS. 4A, 4B, 4C, 5A and 5B show the details of the hardware of the remote control units 3, wherein each unit includes a front panel 230 having the same type of "time remaining" display 4 as that shown and described relative to FIG. 2. Each unit also has a "start" button 32, a "standby/on" LED dsiplay assembly 223, of the same type as in FIG. 2, i.e., green for "standby", red for "on". The emergency stop or "end session" button 35, referenced above, permits the user to be able to terminate the tanning procedure when he chooses, or in case of trouble. In FIG. 4B, it is seen that a housing 240 is adapted to receive the remote control unit panel 230 and is provided with a front mounting plate 241, having an opening 242 to receive the functional subassembly 333 to form the complete remote unit 3. Housing 240 includes metal screw openings 243 to receive metal screws 244 at assembly, as shown in FIGS. 4A & 5B. The back side of housing 240 is seen in FIG. 4C to include elongated openings 245 similar to openings 243, except with an enlarged lower portion and an elongated upper portion to receive the head of a wall mounted screw, for removably hanging the remote control unit 3 near the tanning bed for easy access by the user.

Figure 6:
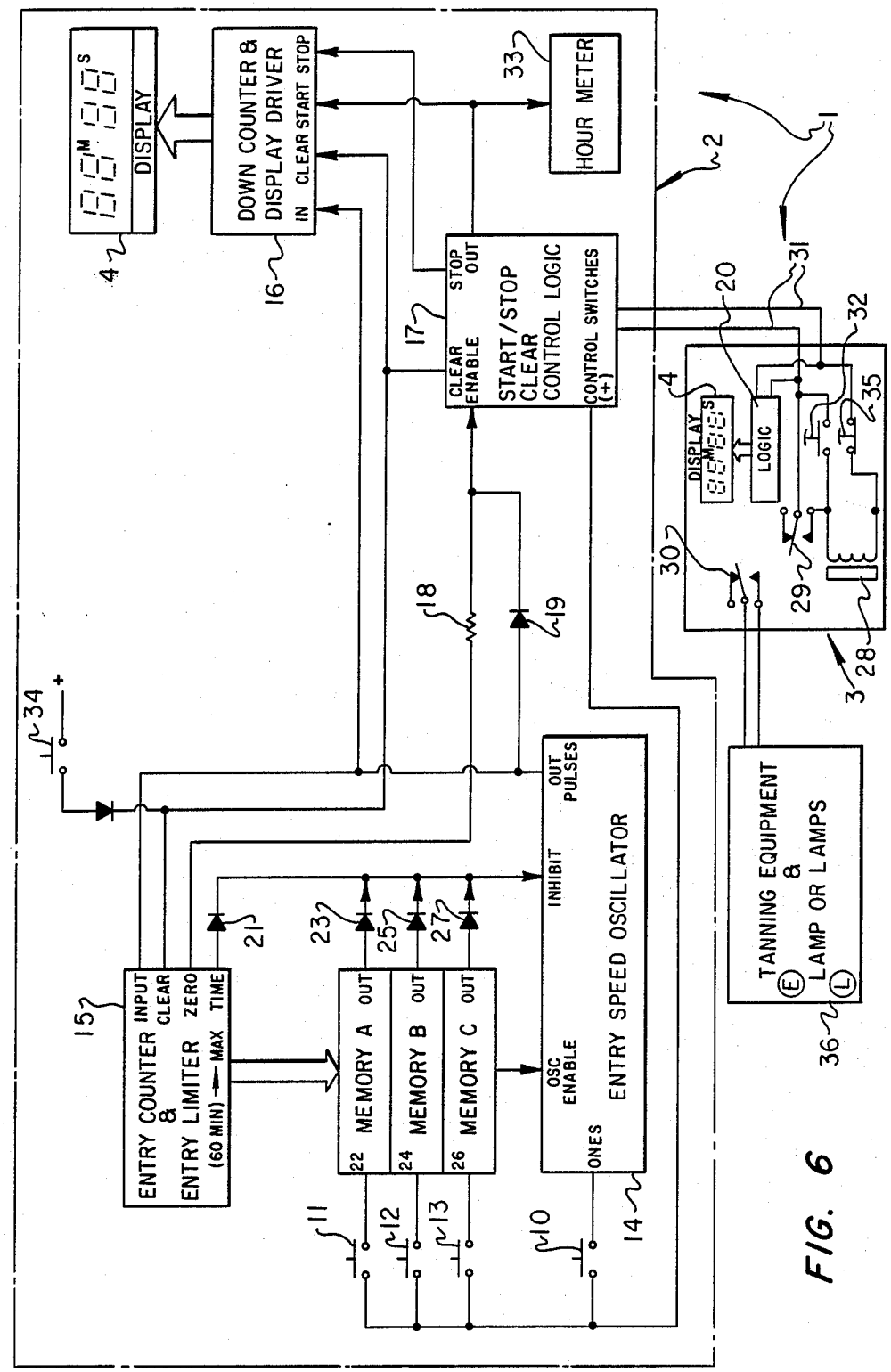
FIG. 6 is a block diagram showing the electronic circuitry of the control elements employed in the equipment of FIG. 1.

FIG. 6 shows a block diagram of the present invention of an electronic control system 1, comprising a main console mounted control unit and circuitry 2, and a remote control and circuitry 3 located near the tanning equipment. Tanning exposure time is entered in minutes into the electronic timer control system 1 manually by depressing pushbutton switch 10 a corresponding number of times to the desired number of minutes to be entered, or, automatically, by depressing one of the momentary action pushbutton switches 11–13, which enters a corresponding preset or memory time into the system.

Each time entry switch 10 is depressed it sends a positive voltage to the one-shot input of the entry oscillator 14, which sends a pulse to entry counter 15, which keeps track of the total minutes entered, and to the "in" terminal of down counter clock/display driver module (or more simply - timer unit) 16.

Entry oscillator 14 also sends a pulse to control logic 17 through diode 19, which in turn, simultaneously sends a pulse through leads 31 to timer unit 20 in remote control unit 3. The display modules 4 will display one minute for each pulse received.

After the first minute is entered into entry counter/entry limiter 15, the zero output changes state, causing a signal which is carried through resistor 18 to the enable input of control logic 17, which places it in the standby mode until time unit 16 times out or until entry is cleared by clear button 34.

A preset or memory amount of time may be entered in automatically by momentarily depressing pushbutton switch 11 for a session length "A", pushbutton 12 for a session length "B", pushbutton 13 for a session length "C", or any one of the three a second time to enter maximum time allowed. Alternatively, additional amounts of time can be added to a preset entry by depressing pushbutton switch 10 the appropriate number of times up to the maximum time setting.

When preset pushbutton 11 is depressed, memory 22 receives and holds the signal, while sending an output to the enable terminal of entry speed oscillator 14, which provides rapid output pulses to the input terminal of entry counter 15 and also to the input terminal of timer units 16 and thorugh diode 19 and control logic 17 and lines 31 to timer 20 and display 4 of remote unit 3. After a certain number of pulses from the output of oscillator 14, determined by a set of selector switches in memory 22, connected to all of the outputs of entry counter 15, memory 22 provides an output through diode 23 to the inhibit input of entry oscillator 14 thus stopping pulses to entry counter 15, timers 16 and 20 at the preprogrammed number determined by the setting of selector switches in memory 22 (e.g. 15 minutes).

Preset pushbutton 12 enters a predetermined amount of time through memory 24 and diode 25. The predetermined time entry is set by selector switches in memory 24 (e.g. session "B" equals 30 minutes). Preset pushbutton 13 enters a predetermined amount of time similarly through memory 26 and diode 27 (e.g. 45 minutes). Additional minutes may be added to any preset entry by depressing switch 10 the desired number of times up to the maximum entry determined by the selector switch in entry counter 15. When maximum entry time is reached (e.g. 60 minutes), continuous output is provided through diode 21 to the inhibit input of oscillator 14 which prevents any additional entrys until timer 16 times out or entry is cleared.

Once any amount of time is entered into entry counter 15, control logic 17 is placed in the standby state which causes it to send a constant DC voltage across the two wires 31 to the remote unit 3, which is now displaying the time purchased and remaining and this permits the tanning equipment to be started by the customer depressing start button 32. When button 32 is depressed momentarily, relay coil 28 energizes and contact 29 closes closes to hold relay coil 28 in such energized state. Relay contacts 30 are also closed by this action to activate the UV lamps in the tanning equipment, indicated at block 36. When coil 28 is energized, a larger current flows through wires 31 which causes control logic 17 to go to the "on" state. At this point, logic 17 sends an output to start timer 16 and hour meter 33, and timer 20 begins its countdown simultaneously.

After the entered amount of time has been counted down to zero, timer 16 sends a signal to the "stop" input of logic 17, and voltage to wires 31 is reduced, and coil 28 is de-energized and contacts 29 and 30 open, which extinguishes the lamps in tanning equipment 36. At this point logic 17 also sends a "clear" pulse to the "clear" terminal of entry counter 15, which thus clears timer units 16 and 20.

A "clear" button 34 on the main unit 2 will clear an entry by resetting entry counter 15, timer 16, logic 17, and through leads 31 to timer 20, reducing all units to the zero state. Switch 34 also functions to stop the countdown mode when the tanning lamps are on, which when depressed momentarily extinguishes the lamps and resets the counters to zero. Emergency stop button 35 on remote unit 3 is a normally closed switch which interrupts power to relay coil 28 when depressed. Stop button 35 will work only when coil 28 is energized and tanning lamps are on and timers 16 and 20 are timing out. Momentarily depressing either 34 or 35 before the timers reach zero will clear the remaining time on both timers and displays and will extinguish the tanning lamps.

Figure 7:
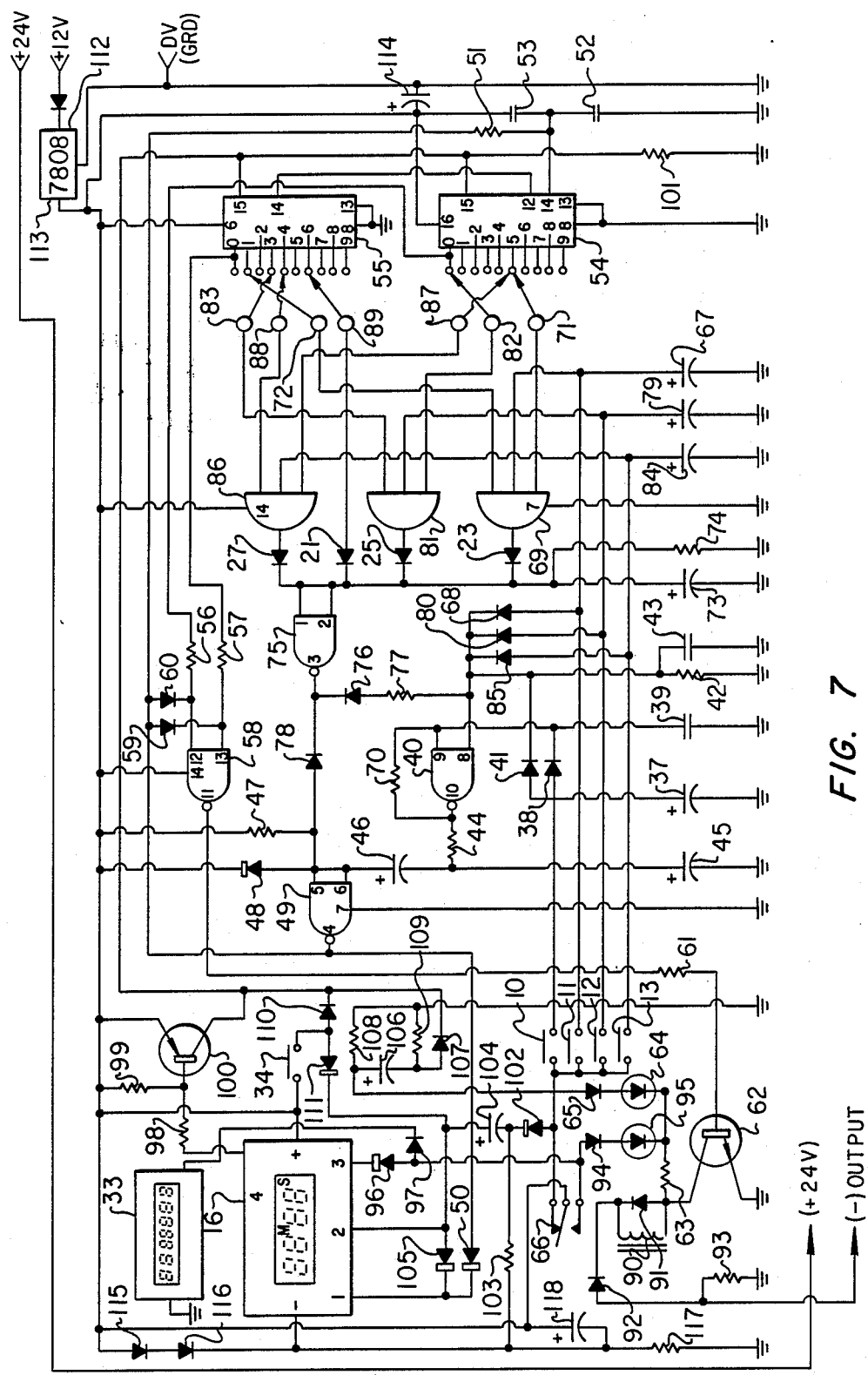
FIG. 7 is a detail circuit diagram of the electronic circuit and components employed in the control unit of FIGS. 1–3.

Referring now in more detail to the circuitry of FIG. 7, exposure time, as paid for by the customer, is entered through normally open momentary pushbutton switches 10, 11, 12 and 13. When switch 10 is manually depressed, a signal is sent to inverter gate 40, capacitor 39, resistor 42 and filter capacitor 43, through diode 38 and diode 41. Invertor gate 40 is a NAND gate, which is a portion of a commercial quad NAND gate (including gates 40, 49, 58 and 75). The inverted signal from gate 40 goes to invertor gate 49 through resistor 44, filter capacitor 46, timing resistor 47 and diode 48. Inverter gate 49 is a NAND gate which is a portion of the same quad NAND gate noted above. Gate 49 provides a timed pulse which goes to the time entry input on clock display module 16 through a low voltage drop diode 50. The output pulse from gate 49 also goes to decade counters 54 and 55 through resistor 51 and filter capacitors 52 and 53. Decade counters 54 and 55, within the Entry Counter/Entry Limiter 15 of FIG. 6, are connected in cascade. They provide ten decoded outputs each. Decade counter 54 keeps track of the "ones" units and decade counter 55 deeps track of the "tens" units that are entered into the timing system. The zero output of counters 54 and 55 are connected to the inputs of inverter gate 58 through resistors 56 and 57 respectively. Gate 58 is a NAND inverter gate which is a portion of the same referenced quad NAND gate. The output of gate 58 goes to the base of NPN transistor 62 through resistor 61. The emitter of transistor 62 is connected to ground and the collector is connected to the cathode of green light emitting diode 64 through resistor 63. The anode of light emitting diode 64 is connected to the supply voltage through diode 65 and relay contacts 66.

A preset amount of time is entered into the system automatically through pushbutton switch 11 which is connected to holding capacitor 67 and inverter oscillator gate 40 through diode 68. gate 40 uses timing capacitor 39 and timing resistor 70 in combination to provide a series of pulses. The output of switch 11 also goes to AND gate 69, which is a portion of three triple input AND gates 69,81 and 86. The other inputs of AND gate 69 are connected to selector switches 71 and 72. Selector switch 71 is connected to the decoded outputs of decade counter 54 and selector switch 72 is connected to the decoded outputs of decade counter 55. The setting of selector switches 71 and 72 determine the prest amount of time entered into the timing system by depressing switch 11. When a signal is applied to all of the inputs of gate 69 simultaneously, an output signal is sent through diode 23 to oscillator output inhibiting inverter gate 75, which also is a portion of the mentioned NAND gate package. The output of gate 75 is connected to the input of gate 49 through diode 78. This output from gate 75 prevents any additional input pulse from being entered into the system through capacitor 46 into gate 49. At this point, clock display module 16 stops at the preset value determined by selector switches 71 and 72, and inverter gate 75 rapidly discharges holding capacitor 67 through diode 76 and resistor 77 and diode 68.

Preset pushbutton 12 also enters a memory time much in the same manner as previously described for pushbutton 11. Whe pushbutton 12 is depressed, holding capacitor 79 is charged sending a signal to oscillator gate 40 through diode 80, and a signal to AND gate 81, also a portion of the mentioned multiple AND gate package. The other inputs of AND gate 81 are connected to selector switch 82, which determines the "ones" units, and selector switch 83, which determines the "tens" units. When counters 54 and 55 reach the preselected value corresponding to the display on clock display module 16 by pulses provided by oscillator gate 40, there is a signal (positive voltage) to all three inputs of AND gate 81, which then sends a positive voltage signal to inverter gate 75 through diode 25, which ends the up count entry process. Inverter gate 75 also rapidly discharges holding capacitor 79 through diode 76, resistor 77 and diode 80.

Preset pushbutton 13 enters a preset time into the system in the same manner as pushbutons 11 and 12. When pushbutton 13 is depressed, holding capacitor 84 is charged, and a positive voltage signal is applied to oscillator gate 40 through diode 85, and a signal is also applied to AND gate 86, (of the AND gate package). Oscillator gate 40 provides pulses through inverter gate 49, which advances clock display module 16 and counters 54 and 55.

The other two inputs of gates 86 are connected to selector switch 87; which determines the preset "ones" units, and to selector switch 88, which determines the preset "tens" units. When counters 54 and 55 reach the preselected value, there is a signal to all three inputs of AND gate 86, which in turn sends a signal to inverter 75 through diode 27. The output from gate 75 inhibits the output from oscillator gate 40 through deiode 78, preventing any additional upcount entry pulses from being added into the counters. The output of inverter gate 75 also discharges holding capacitor 84 through diode 76, resistor 77, and diode 85, which together with capacitor 84 cause gate 40 to oscillate. As entry pulses are put into the counters, transistor 62 correspondingly opens and closes with the pulses. This is accomplished by the output of gate 49 connected to the inputs of gate 58 through diodes 59 and 60. Gate 58 biases transistor 62 through resistor 61.

After the pulses have been entered into the clock module 16, the transistor 62 is then switched on and stays on until the remaining time is activated and "times out", or until entry has been cleared. Transistor 62 supplies a ground to relay coil 90. Diode 91 absorbs back EMF from relay coil 90. The other side of relay coil 90 is connected to the remote control unit 3 through diode 92. Resistor 93 supplies a small current to the remote control unit 3 at all times, even when transistor 62 is switched off. When the start button 32 is depressed on the remote unit 3, the circuit is completed across wire pair 31, supplying current to energize relay coil 90, which, when energized closes contacts 66 to supply a positive voltage to the start input of clock display module 16 through diode 96 and to hour meter 33 through diode 97. A positive voltage is also applied to the anode of red light emitting diode 95 through diode 94. At this point the green LED circuit is switched off. The cathode of LED 95 is connected to resistor 63 and transistor 62 to ground.

With the tanning equipment 36 switched on, the display clock module 16 begins its count down. When the clock module 16 reaches "0", an output is given through resistors 98 and 99 to transistor 100. This output causes transistor 100 to conduct and send a positive voltage to resets of decade counters 54 and 55 across resistor 101. Decade counters 54 and 55 then both give a "0" output, which goes through resistors 56 and 57 respectively to gate 58, causing it to change state and switch transistor 62 off through resistor 61. Relay coil 90 de-energizes and relay contact 66 opens. A reset pulse is also sent through diode 102 and capacitor 104 and diode 105 to the reset inputs (1) and (2) of clock display module 16. A reset pulse is also sent to decade counters 54 and 55 through capacitor 106 and diode 107 across discharge resistors 108 and 109, and 101.

The displays and counters can be cleared at any time by pressing the "clear" pushbutton switch 34, whether the unit is in the "standby" or "on" state. A positive voltage is sent to the reset inputs of decade counters 54 and 55 through diode 110. A positive voltage is also sent to the reset input of clock display module 16 through diodes 111 and 105. If tanning lamps L are on at this point, they will be extinguished.

The circuit receives power from a class 2, plug-in transformer, not shown, which supplies the circuit with a +12 volts, and a +24 volts power input. The main circuit is operated by 12 volts, regulated to +8 v, and the remote control circuit is operated by +24 volts. The incoming 12 volts to the main circuit is supplied through input protection diode 112 to an on-board, three terminal, 8 volt regulator 113, which is connected to a filter capacitor 114. The clock display module 16 is operated on 1½ v, which is supplied through a regulator comprised of diodes 115 and 116, and resistor 117 and filter capacitor 118.

FIG. 7A shows an addition to the circuit of FIG. 7 which may be employed if desired, to use an LED 151 to provide a flashing yellow light in control unit 2 to signify that the session is over and the tanning room may require maid service. When timer 16 sends a signal from its terminal (4) that the time has expired, the flip-flop 152 is actuated to pulse LED 151, which will continue until the flip-flop is reset by a signal from switch 34.

FIG. 8 shows the circuit of the remote control unit 3, a voltage regulator comprised of resistor 119, Zener diode 120, diodes 121 and 122, filter capacitors 123 and 124, which supply the remote circuit with power of 5 volts to the logic circuitry of module 20 of the remote control unit 3, and 1½ volts to clock display circuitry of modules 4. Pulses across wires 31 to the input of the remote control unit 3 are sent through resistor 125, Zener diode 126, and photo darlington style opto-coupler 127. Pulses sent through opto-coupler 127 go across resistor 128 to one-shot inverter gate 132 through timing capacitor 129, timing resistor 130, and diode 131. Gate 132 is one portion of a quad NAND gate (only three portions used in this circuit). It acts as a one-shot oscillator, which applies the pulses to the input of clock display module 10 through diode 133. Gates 137 and 142 are reset gates which are each a portion of the same quad NAND gate.

When the presence of a voltage or a signal is undetected by the photo transistor in opto-coupler 127, capacitor 136 begins to charge through resistor 134, and discharge through diode 135 if a pulse is present. If there is no pulse or voltage for a period longer than ½ second, gate 137 will change states. The output of gate 137 goes through resistor 138, timing capacitor 139, timing resistor 140, and diode 141 to gate 142, which provides a short pulse to the reset inputs (1) and (2) of clock module 20 through diodes 143 and 144. This hook-up causes the remote display 20 to show exactly the same information as clock display module 16 in the main control unit 2.

When a voltage is present across the inputs of the remote unit 3, the timers 16 and 20 can be started by depressing start button 32 momentarily, which causes relay contacts 29 to close, thus holding relay 28 energized. This action also carries a current to relay coil 90 through transistor 62 in the main control unit to start the timer 16 in the main console M. Diode 148 is installed across the relay coil 28 to absorb any back EMF.

When relay contacts 29 close, light emitting diode 146 of 223 illuminates when completing the circuit through resistor 147 to ground. When relay coil 28 energizes, relay contacts 30 also close, supplying a power switch or plug 340 to supply utility line 300 power, usually 110 v or 220 v, to the lamps and tanning equipment, indicated at 36 in FIG. 6. When relay contacts 29 close, they also send a signal to the start input (3) of clock display module 20 through diode 145, and the countdown, emergency stop button 35 can be depressed to end the tanning session before the time is up. If this button 35 is depressed, or display modules 16 and 20 reach "0", relay coils 28 and 90 de-energize and rest all circuits to their "off" or zero state, and power to the tanning equipment 36 is switched off by the opening of relay contacts 30.

Other operating components in the control circuit of main console unit 2 include selector wwitch 89 which determines maximum entry time limit (eg. 60 min), so that when decade counter 55 has reached the maximum time set, a positive voltage passes from decade counter 55 through selector switch 89 and through diode 21 to activate inhibit gate 75, which prevents any additional up count timer pulses from being entered into timers 16 & 20. Other components utilize primarily to enhance the overall performance of the timing system are: filter capacitor 45 smooths the output of osciIator 40; capacitor 37 debounces the output from switch 10; the combination of capacitor 73 and resistor 74 holds the output from any of the memory gates (eg. 69, 81 or 86) until it's corresponding capacitor (eg. capacitor 67,79, or 84) is discharged; resistor 103 functions to hold capacitor 104 in the discharged state and electrolytic capacitor 114 functions as a power supply filter capacitor for the 8 volt output from regulator 113.

The invention herein is not limited to the specific embodiment shown, but rather to that which falls within the scope of the appended claims:

What is claimed is:

1. A tanning studio having a tanning system, including a main control console unit for operation only by an attendant, and a remote control tanning room unit for operation only by a patron, and tanning equipment and lamps in said tanning system, comprising:
    a. a module setting and displaying the time remaining for use of the tanning equipment and system on both the console and the remote unit, which time is below an identified safe maximum time limit inherent in said system,
    b. means on said console unit only to input the initial time remaining for use of said tanning equipment and system,
    c. means on said remote unit only to actuate said tanning equipment and system,
    d. and means on both said console unit and said remote unit to clear the time remaining for use of the tanning equipment and system, and to extinguish the lamps therein,
    e. and a downcount timer on each of said units for continuously displaying the time remaining in a descending operating mode.

2. A tanning system as in claim 1, wherein said last named means in each unit acts simultaneously to clear the time remaining and to extinguish said lamps.

3. A tanning system as in claim 1, wherein said means are electronic and employ electrical circuits, and wherein the total electrical circuit connection between said console unit and said remote unit comprise two conductors.

4. A tanning studio having an operator, and including a tanning system with a main console control unit and a remote tanning room control unit, including tanning equipment and lamps for use by a patron, comprising:
    a. a module for setting and displaying the time remaining for use of the tanning equipment on both the console unit and on the remote unit, which time is at or below the legal limit set by the applicable governmental agency for patron safety,
    b. means on said console unit only to permit input of the initial time remaining solely by the operator, for the use of said tanning equipment and system,
    c. means on said remote unit only to actuate said tanning equipment at the sole option of the patron,
    d. and means on both said console unit and said remote unit to clear the time remaining for use of the tanning equipment and system, and to extinguish the lamps therein,
    e. a downcount timer on each of said units for continuously displaying the time remaining in a descending operating mode, and
    f. means to separately indicate to the operator when the tanning equipment is not in use and is available for maintenance or for additional patron use.

5. A tanning system as in claim 4, wherein the entire electrical contact between said module and said remote control unit comprises only two electrical conductors, each of which transmits signals to and from each of the units in this combination.

* * * * *